United States Patent

Gustafsson et al.

[11] Patent Number: 5,250,762
[45] Date of Patent: Oct. 5, 1993

[54] LOAD CELL HOUSING HAVING TILTABLE CONTACT BODIES ON OPPOSITE SIDES THEREOF

[76] Inventors: Pär Gustafsson, Liljanstorpsvägen 76, S-722 46 Västerås; Ake Persson, Humlegatan 35 C, S-722 26 Västerås, both of Sweden

[21] Appl. No.: 817,492

[22] Filed: Jan. 7, 1992

[51] Int. Cl.⁵ ............................................. G01G 21/28
[52] U.S. Cl. ................................... 177/244; 177/225; 177/229; 177/211
[58] Field of Search ............... 177/244, 211, 225, 229

[56] References Cited

U.S. PATENT DOCUMENTS

| | | | |
|---|---|---|---|
| 4,554,987 | 11/1985 | Dillon | 177/134 |
| 4,606,421 | 8/1986 | Schroeder | 177/211 |
| 4,616,723 | 10/1986 | Pietzsch et al. | 177/211 |
| 4,653,599 | 3/1987 | Johnson | 177/211 |
| 4,655,306 | 4/1987 | Sauer | 177/229 |
| 4,765,423 | 8/1988 | Karpa | 177/211 |
| 4,775,018 | 10/1988 | Kroll et al. | 177/211 X |
| 4,804,053 | 2/1989 | Nordstrom | 177/211 |

Primary Examiner—Benjamin R. Fuller
Assistant Examiner—R. Gibson

[57] ABSTRACT

For measuring tensile force in a continuous strip or web, load cells are arranged between a bearing housing for a deflector roll, over which the web runs, and a fixed base. A load cell comprises a load cell housing and consists of two yokes (1, 2) facing the bearing housing and the base, respectively, and a force transducer which together with membranes (3 ... 6) are arranged between the yokes to connect these together. At the end plates of the yokes, screw holes (8 ... 15) are provided to attach the yokes to the bearing housing and the base, respectively. At each screw hole there is provided a gap (16) so that, around each screw hole, a tubular body is formed and that the plane outwardly-facing surfaces (17) of the bodies are plane-parallel and extend outside the otherwise plane outwardly-facing surfaces of the yokes.

3 Claims, 1 Drawing Sheet

LOAD CELL HOUSING HAVING TILTABLE CONTACT BODIES ON OPPOSITE SIDES THEREOF

TECHNICAL FIELD

Within, inter alia, the paper, plastics, textile and metal industries, the tensile force and/or the tensile stress in the continuous material web or strip are often measured to indicate, monitor and control the manufacturing process. The measurement is normally performed in such a way that the continuous web is allowed to pass through a deflector roll. Between the bearing of the deflector roll and the base there are arranged load cells comprising a load cell housing with a built-in transducer of preferably magnetoelastic type. The invention relates to a special design of the housing to avoid internal bending moments and stresses in the housing because of the attachment to both the base and the bearing of the deflector roll.

BACKGROUND ART, THE PROBLEM

To understand the importance of a good constructive design of the load cell housing, a short description of the measurement of tensile force and/or tensile stress will first be given. The deflector roll is journalled in a conventional manner in a bearing housing. Between the bearing housing and the base, that is, some kind of foundation, the load cell housing is placed. This substantially consists of two relatively stiff parallelepipedic yokes, one of which makes contact with the bearing housing and the other makes contact with the base. The yokes are connected together by a number of membranes and a transducer in such a way as to make possible a certain movability in the longitudinal direction of the yokes. The transducers are oriented such that only the force $F_r$ in the direction of movement, that is, normally in a horizontal direction, is measured. With knowledge of the angle of entry and the angle of departure of the continuous web at the deflector roll in relation to the direction of movement mentioned, the tensile force $F_d$ in the continuous web can be calculated in a simple manner. With knowledge of the cross section area of the continuous web in question, also the tensile stress can thus be determined.

The insertion of a transducer parallel to the above-mentioned membranes between the two yokes can normally be performed in such a way that no measurable forces arise in a direction parallel to the two yokes. Nor are there any major problems from the manufacturing point of view in making the outer plane sides of the two yokes plane-parallel.

An additional condition for obtaining a good accuracy is that the side of the bearing housing which faces the yoke of the load cell housing has a plane surface. The same demands are also placed on that surface of the base which faces the other yoke of the load cell housing. To be able to meet the given accuracy data, specified planeness requirements are often indicated.

It is also very important always to mount the load cell at an angle of exactly 90° with the deflector roll to prevent any lateral forces from getting into the direction of measurement.

The attachment of the load cell housing to the bearing housing and to the base, respectively, is often carried out using screws which from the side of the bearing housing and the base, respectively, are screwed into threaded holes in the yokes. Although normally specified tightening moments are prescribed for the screwing, it has proved that the attachment of the load cell housing often influences the accuracy of measurement in a very negative way because internal bending moments and forces of no inconsiderable magnitude may then arise in the load cell housing. This manifests itself in such a way that a load cell senses a tensile force in a direction parallel to the yokes without there being any continuous web on the deflector roll.

Various designs of the yokes have been presented in order to reduce the above-mentioned problem. Instead of allowing the outer plane-parallel surfaces of the yokes to make close contact with the bearing housing and the base, respectively, it is possible to provide the plane surfaces of the yokes with narrow grooves parallel to the shaft of the deflector roll and placed on respective sides of the threaded holes. Such grooves are shown, inter alia, in figures in the ABB pamphlet PillowBlock tensiometer, A07-7505 E. Otherwise, this pamphlet shows the construction of a complete load cell and how this is integrated into a production plant for a continuous web where the tensile force or the tensile stress in the web need to be measured. The transducer used in this case consists of a magnetoelastic transducer which, by a suitable location of holes for an excitation and measuring winding, only measures the force in the longitudinal direction of the yokes.

Although the introduction of the above-mentioned grooves has entailed improvements in relation to the plane-parallel outer yoke sides, the problems have not disappeared entirely. The basic reason for these problems arising is, as mentioned above, that the tightening of the screws gives rise to internal bending moments and stresses in the yokes which may result in the load cell sensing a tensile force in a direction parallel to the yokes without there being any continuous web on the deflector roll. The technical explanation of the occurrence of bending moments in the yokes is that the contact surface around each screw in the present designs does not provide a symmetrical counter-support. By symmetrical counter-support is meant here that if the contact surface around each screw hole is conceived to consist of a large number of surface elements, then the sum of the "surface moments" of the surface elements, that is, the respective surface element area multiplied by its surface pressure and the distance to the screw centre, should be zero. Since neither the design solution with plane-parallel outer yoke sides, nor outer yoke sides with grooves exhibits a symmetrical counter-support, there will always be internal bending moments and associated mechanical stresses in the yokes.

SUMMARY OF THE INVENTION, ADVANTAGES

The invention constitutes a constructive design of the area around the screw holes of the yokes which practically allows symmetrical counter-supports for all screw connections between the yokes and the bearing housing and the base, respectively. This means that the influence on the measurement of tensile force and tensile stress in the continuous web exterted by the attachment of the yokes, that is, internal bending moments and mechanical stresses in the yokes, is practically eliminated.

The screw holes may either be threaded along the whole length or be threaded from the outer plane surfaces of the yokes only to such an extent into the yokes as is needed to ensure, with a certain margin, sufficient prestress in the screws. From the outer, outwardly-facing plane of the yokes there is provided, at each screw hole, a gap with a depth into the yoke which is sufficient to reduce the effect of stresses arising from the mounting of the load cell to a level permissible for each particular case. Normally, this means that the depth is larger than one-fourth of the screw hole diameter. The outwardly-facing plane surface of the tubular body thus formed around the screw holes lies somewhat outside the otherwise outer plane surfaces of the yokes. The cross section area of the body, for example as regards the outer periphery towards the gap, may be in the form of a polygon or be circular. The yokes are normally provided with four screw holes which are placed, in pairs, parallel to and near the end plates of the yokes. This means that the two yokes of the load cell housing will have, as contact surface with the bearing housing and the base, respectively, four plane surfaces centered around the screw holes. Because the tubular bodies, which now form coupling elements between the yokes and the bearing housing and the base, respectively, may be compressed axially and expand outwards during the mounting, counting from the centre line of the screw hole, practically independently of the adjacent parts of the yokes, only a minimum deformation caused by internal moments and mechanical stresses will arise in the yokes.

The external dimensions of the tubular bodies must be chosen in such a way that the stresses from the contact pressure between the plane surfaces and the bearing housing and the base, respectively, is well within the allowable limits.

Generally, however, it is desirable to minimize the contact surface of the load cell housing with the surroundings. This reduces the risk of foreign particles or irregularities of the base giving rise to internal bending moments or mechanical stresses in the yokes. This was also the idea behind the introduction of the grooves, described above under "Background art, The problem". However, this did not afford the advantage of the symmetrical counter-supports, provided by the tubes.

From the point of view of lateral load, it is desirable for the two screw attachments, which are located at the end plates of the yokes, to be located as far out towards the longitudinal sides of the yokes as possible. Since, of course, equilibrium of moments must prevail between the force-absorbing contact surfaces of the yokes and the lateral load, the load on the coupling elements will be lower as the distance increases. In the design using grooves, however, there is a contact surface between the screws which is of no use.

To render the yokes still more adaptable to, inter alia, a possible level difference or irregularity of the base and the bearing housing, respectively, at the contact surfaces of the screw pairs, the tubular bodies may be provided with one or more waists, thus reducing the flexural rigidity of the bodies. This will be clarified in the description of the different embodiments. By the waists the bending moment, which arises in the bodies in the case of an uneven base, will be reduced. An advantage of the reduced bending moment is that the effect on the yokes in the form of internal stresses and moments in the yokes will be reduced. The waists may be produced in different ways by reducing the material in the tube wall.

DESCRIPTION OF THE PREFERRED EMBODIMENTS

Figure 1:
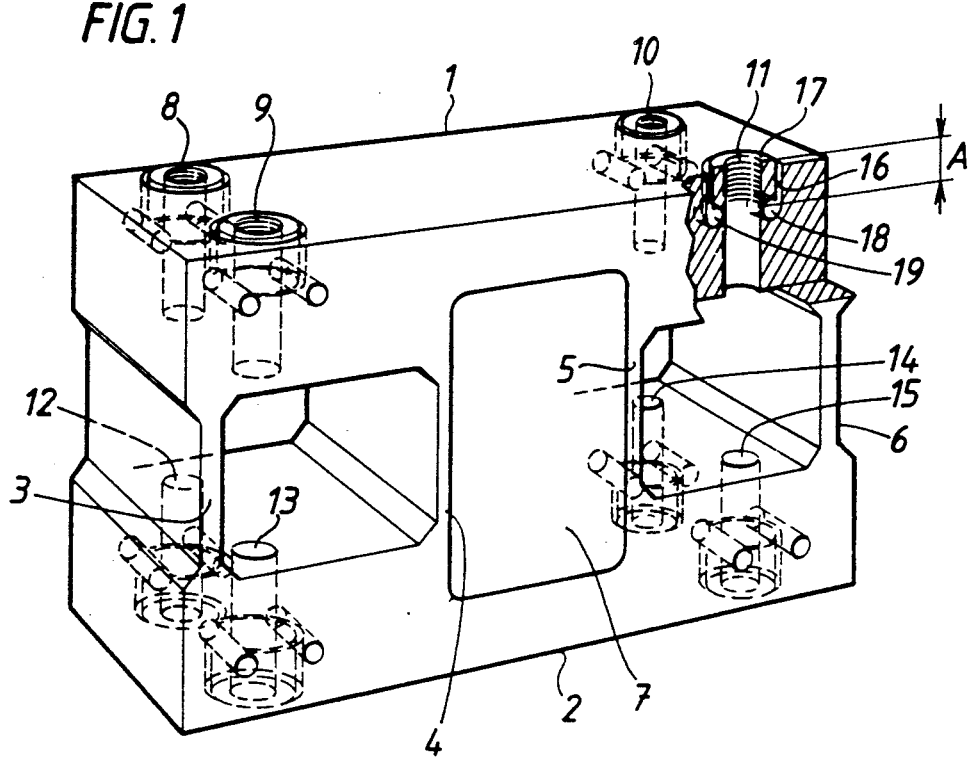
FIG. 1 shows a load cell according to one embodiment of the invention.
Figure 2:
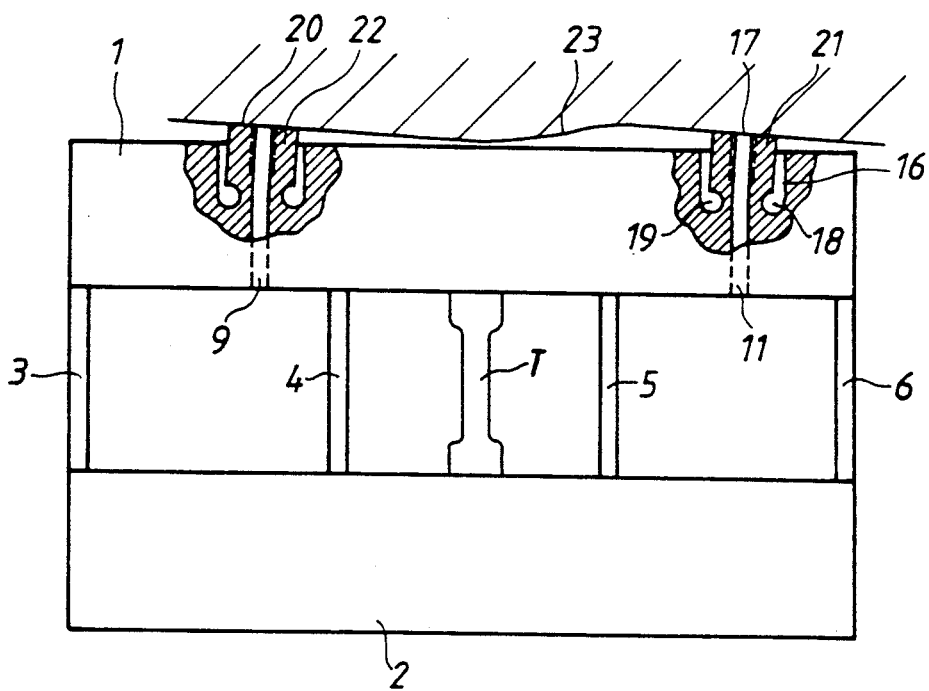
FIG. 2 shows how the waists facilitate the adaptation of the tubular bodies to an uneven base.

A preferred embodiment of the invention is shown in FIGS. 1 and 2 which shows a complete load cell comprising a load cell housing and a built-in load transducer. The load cell housing consists of two substantially parallelepipedic yokes 1 and 2 interconnected by the membranes 3, 4, 5 and 6. Behind the cover plate 7 and parallel to the membranes a force transducer (not shown) is mounted and applied in such a way that only the force in the longitudinal direction of the yokes is measured. In the embodiment of the load cell housing shown, both yokes are provided at their end plates with two screw holes 8 ... 15 for attachment against a force-introducing device (not shown) in the form of a bearing housing and a base, respectively. All the screw holes and the nearest part of the yokes are formed in the same way as illustrated by the sectional view at the screw hole 11. As will be clear, viewed from the plane outer surfaces of the yokes, the screw holes are threaded a distance A. In a preferred embodiment according to the example shown in FIG. 1, the gaps are formed circularly concentrically with the threaded holes with a depth somewhat larger than that of the threaded depth. In order not to overload FIG. 1 with too many reference numerals, reference is only made in FIG. 1 to the gap 16 around the screw hole 11. As will also be clear, the annular, outwardly-facing plane surfaces 17, which are a result of the circular tubular bodies shown in the example, extend somewhat outside the remaining outer plane surfaces of the yokes. The contact surface of the two yokes with the bearing housing and the base, respectively, will therefore consist of four plane surfaces arranged annularly around the screw holes.

In an alternative embodiment of the invention, each tubular body consists of a separate both centrically and, at least to a certain extent, externally threaded body. Holes are therefore provided in the yokes which are threaded with threads corresponding to the external threads of the bodies. To obtain the desired gap, the hole nearest the outer plane surfaces of the yokes is made with a correspondingly larger diameter.

Within the scope of the invention, the outer periphery of a cross section of the tubular body, besides being formed as a circular periphery as mentioned above, may be formed in a plurality of different ways which as far as possible satisfy the requirements for symmetrical counter-supports. The periphery of the cross section of the body may, for example, be formed as a polygon or as parts of a circle and one or more chords. The latter will be the case if the centre of the screw holes is located so close to the longitudinal sides and the end plates of the yokes that the radius of the tubular body is larger than the distance between the centre of the screw hole and the longitudinal sides and the end plates, respectively.

As described above, the yokes can also be made more adaptable to a possible level difference or irregularity of the base and the bearing housing, respectively, close to the contact surfaces of the screw pairs by providing the tubular bodies with one or more waists. In a preferred embodiment, the waists are formed, as will be clear from the example shown in FIG. 1, by providing, on both longitudinal sides, at a distance from the outer plane surfaces of the yokes and symmetrically in relation to the centre line of the screw hole, for each screw hole two straight inwardly-directed cylindrical recesses 18 and 19 which may preferably be of circular cross section. The recesses are so dimensioned that those generatrices of the recesses which are located furthest away from the centre line of the screw hole at least touch the outer periphery of the tubular bodies formed around the holes.

FIG. 2 shows how the waists allow an adaptation of the end surfaces 17 and 20 of the tubular bodies 21 and 22 to a bearing housing 23 with an uneven surface facing the yoke 1 (the surface being enlarged for the sake of clarity).

The scope of the invention allows for several alternative embodiments and locations of the waists. As already indicated, each one of the bodies may be provided with only one waist. The waists may also be made as holes extending from the end plates of the yokes towards the bodies. Although it is advantageous, from the point of view of manufacturing, with a circular cylindrical embodiment of the waists, also other embodiments may be used.

We claim:

1. A load cell housing which comprises first and second parallelepipedic yokes and a plurality of membranes connected therebetween, said first and second yokes defining planar surfaces on outwardly facing sides thereof and a plurality tubular bodies that project beyond said planar surfaces and provide flat contact surfaces, said first and second yokes defining gaps around said tubular bodies to allow said tubular bodies to individually tilt and conform to an uneven support surface.

2. A load cell housing according to claim 1, wherein said first and second yokes define waists at bottoms of said gaps.

3. A load cell which comprises:
a housing that includes first and second parallelepipedic yokes and a plurality of membranes connected therebetween, said first and second yokes defining planar surfaces on outwardly facing sides thereof and a plurality tubular bodies that project beyond said planar surfaces and provide flat contact surfaces said first and second yokes defining gaps around said tubular bodies to allow said tubular bodies to individually tilt and conform to an uneven support surface, and
a force transducer positioned between two of said membranes and extending between said first and second yokes.

* * * * *

UNITED STATES PATENT AND TRADEMARK OFFICE
CERTIFICATE OF CORRECTION

PATENT NO. : 5,250,762
DATED : October 5, 1993
INVENTOR(S) : Pär Gustafsson et al.

It is certified that error appears in the above-identified patent and that said Letters Patent is hereby corrected as shown below:

On the title page, the following should be inserted:

[30] Foreign Application Priority Data

Feb. 25, 1991 [SE] Sweden ........ 9100537

Signed and Sealed this

Twenty-ninth Day of March, 1994

Attest:

BRUCE LEHMAN

Attesting Officer      Commissioner of Patents and Trademarks